United States Patent [19]

Tanaka et al.

[11] Patent Number: 5,286,625
[45] Date of Patent: Feb. 15, 1994

[54] METHOD FOR ASSAYING ENDOTOXIN IN A WHOLE BLOOD SAMPLE OR PROTEIN SOLUTION CONTAINING THE SAME

[75] Inventors: Shigenori Tanaka; Hiroshi Tamura, both of Tokyo, Japan

[73] Assignee: Seikagaku Corporation, Tokyo, Japan

[21] Appl. No.: 789,583

[22] Filed: Nov. 8, 1991

[51] Int. Cl.$^5$ .............. C12Q 1/34; C12Q 1/00; C12Q 1/37; G01N 1/00
[52] U.S. Cl. ..................... 435/18; 435/4; 435/23; 435/24; 436/175
[58] Field of Search ............. 435/18, 4, 23, 24; 436/175

[56] References Cited

U.S. PATENT DOCUMENTS

| | | | |
|---|---|---|---|
| 4,406,832 | 9/1983 | Mills | 260/112.5 R |
| 4,495,294 | 1/1985 | Nakahara | 436/502 |
| 4,510,241 | 4/1985 | Mills | 435/23 |

OTHER PUBLICATIONS

H. Tamura et al., "A New Sensitive Method for Determining Endotoxin in Whole Blood", *Clinica Chimica Acta*, 200:35-42 (1991).

*Primary Examiner*—Michael G. Wityshyn
*Assistant Examiner*—Ralph Gitomer
*Attorney, Agent, or Firm*—Sughrue, Mion, Zinn, Macpeak & Seas

[57] ABSTRACT

A method of assaying an endotoxin using the limulus amebocyte lysate component which comprises pretreating whole blood with nitric acid and a surfactant selected from among polyoxyethylene ethers represented by the following formula:

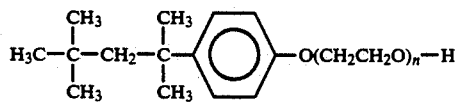

wherein n is an integer of from 8 to 40; or:

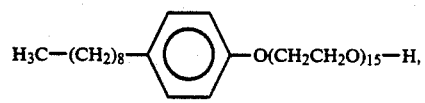

polyoxyethylene sorbitans, n-alkylglucopyranosides, sodium dodecylsulfate and lithium dodecylsulfate, which enables an efficient and accuate assay of an endotoxin.

8 Claims, No Drawings

METHOD FOR ASSAYING ENDOTOXIN IN A WHOLE BLOOD SAMPLE OR PROTEIN SOLUTION CONTAINING THE SAME

FIELD OF THE INVENTION

This invention relates to a process for assaying an endotoxin. More particularly, it relates to a process for assaying an endotoxin efficiently at a high accuracy.

BACKGROUND OF THE INVENTION

There has been known a process for assaying an endotoxin contained in a vital sample with the use of a component of limulus amebocyte lysate [limulus test (LAL-Test)]. For example, U.S. Pat. No. 4,495,294 corresponding to JP-B-63-55671 discloses an assay method wherein a vital sample containing protein cell granules (for example, plasma, serum, albumin, globulin, ascites, articular fluid or external or internal exudation or excretion such as urine), which has been treated with an acid having a pKa of 3 or less at 25° C. at pH 3 or below, is assayed with the use of the limulus amebocyte lysate component (the term "JP-B" as used herein means an "examined Japanese patent publication").

However, it is found that the detection ratio of an endotoxin in whole blood assayed by the method described in the aforesaid patent is not as high as expected (i.e., 50 to 60%).

Under these circumstances, the present invention aims at providing a process for efficiently assaying an endotoxin in whole blood at an extremely high detection ratio.

On the other hand, there has been known that it is very difficult to accurately assay an endotoxin in a protein solution.

The present invention further aims at providing a process for accurately assaying an endotoxin contained in a solution of, for example, protein, protease or protease inhibitor.

SUMMARY OF THE INVENTION

According to the present invention, the aforesaid problem has been solved by assaying a specimen, which has been prepared by treating whole blood or a protein solution with a surfactant selected from polyoxyethylene ethers represented by formulae:

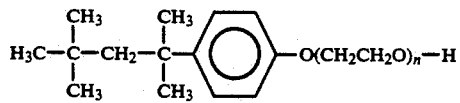

wherein n is an integer of from 8 to 40; or:

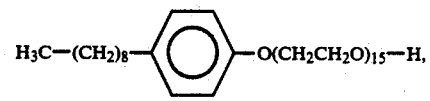

polyoxyethylene sorbitans, n-alkylglucopyranosides, sodium dodecylsulfate and lithium dodecylsulfate and nitric acid, by using the limulus amebocyte lysate component.

DETAILED DESCRIPTION OF THE INVENTION

Examples of the polyoxyethylene ethers to be used as a surfactant in the present invention include polyethylene glycol mono-p-iso-octylphenyl ether, polyethylene glycol mono-p-tert-octylphenoxypolyethoxyethanol and polyethylene glycol mono(nonylphenyl) ether. Examples of the n-alkylglucopyranosides include n-(octyl-, nonyl-, dodecyl-, decyl- or heptyl) ($\alpha$- or $\beta$-)-D-glucopyranoside. Examples of the polyoxyethylene sorbitans include polyoxyethylene sorbitan monolaurate, monopalmitate, monostearate, monooleate and trioleate. Preferable surfactants are polyethylene glycol mono-p-iso-octylphenyl ether, polyoxyethylene sorbitan monolaurate, polyoxyethylene sorbitan monooleate, dodecylsulfate, and n-octylglucopyranoside.

The present invention is characterized in that whole blood is treated with the above-mentioned surfactant and nitric acid. It is preferable to add the surfactant to the whole blood so as to give a final concentration of 0.08 to 0.33% (w/v). On the other hand, nitric acid may be preferably added to the whole blood so as to give a final concentration of 0.28 to 0.83 mol/l.

The treatment of the whole blood with the surfactant and nitric acid may be preferably effected at 4° to 80° C., preferably 25° to 70° C., more preferably 37° to 60° C. for 3 to 30 minutes, more preferably for 5 to 30 minutes.

The whole blood may be treated with the surfactant and nitric acid as follows. Namely, the whole blood may be treated with the surfactant and then with nitric acid. Alternatively, it may be treated with the surfactant and nitric acid simultaneously. Alternatively, it may be treated with a nitric acid solution containing the surfactant.

According to the present invention, a specimen, which has been prepared by treating whole blood with a surfactant and nitric acid, is assayed with the limulus amebocyte lysate component. Highly preferable assay results can be achieved by adjusting the pH value of the specimen within a range of from 5 to 9.

In the present invention, furthermore, an endotoxin contained in a protein solution can be accurately assayed by adding whole blood to the protein solution prior to the pretreatment with a surfactant and nitric acid and then treating it by the same method as the one described above.

The whole blood sample or protein solution sample pretreated as described above can be applied to a known limulus test such as a method of determining a detection ratio of an endotoxin added to the sample (J. Lab. Clin. Med., 104, 321, 1984), the turbidimetric method comprising measuring the increasing turbidity during the gelation reaction (Appl. Environ. Microbiol., 41, 1316, 1981), the turbidimetric kinetic assay comprising measuring turbidity change in gel-clotting and determining the gelation time (J. Parent. Sci. Technol., 39, 194, 1985), and the quartz chemical analysis comprising determining the change of the resonant frequency according to coagulation (gelation) (Proc. of MRS Int'l. Mtg. on Adv. Mats., 14, 221, 1989).

An endotoxin in the protein solution can be determined by subtracting the amount of the endotoxin in the whole blood from the total amount of the endotoxin detected.

The "whole blood" to be used in the present invention generally means animal blood. Examples thereof include human, bovine, equine, canine, sheep, goat, rabbit, rat, guinea pig and mouse bloods.

The limulus amebocyte lysate component used in the present invention is obtained by collecting blood lympha from horseshoe crab such as *T. tridentatus* in Japan, *T. gigas* in Thailand and Malaysia, *L. polyphemus* in U.S.A., and *C. rotundicauda* in Thailand and Malaysia, then fracturing blood cells followed by separating a lysate component. A lysate component derived from *T. tridentatus* is preferably used.

The present invention is characterized in that whole blood to be assayed for an endotoxin with the limulus amebocyte lysate component is pretreated with a specific surfactant and nitric acid to serve as a specimen.

Although the mechanism of the assay process of the present invention has never been clarified in detail hitherto, it is assumed that the assay proceeds as follows. Namely, it is known that endotoxin receptors are present on the surface of erythrocytes, platelets, leukocytes and B-cells contained in the whole blood. It is considered that these endotoxin-binding receptors adsorbed on the surface of the above-mentioned cells are efficiently liberated by treating the whole blood with a specific surfactant and nitric acid.

The present invention is described in detail below with reference to the following Examples and Comparative Examples, which are not construed to limit the scope of the present invention.

EXAMPLE 1

0.5 ml of an anticoagulant [7.6% (w/v) of sodium citrate] was added to 10 ml of whole blood collected from a healthy subject. Then the whole blood was frozen at $-80°$ C. for a short period and then completely hemolyzed to serve as a whole blood sample.

To 0.1 ml of this whole blood sample was added 0.01 ml of an aqueous solution containing 30 pg of an endotoxin preparation from *E. coli* 0111:B4 (Difco Laboratories, Inc.). Then, 0.5 ml of an aqueous solution of nitric acid of a definite concentration containing 0.25% by weight of a surfactant Triton X-100 (polyethylene glycol mono-p-iso-octylphenyl ether, product of Rohm & Hass Co.) was added thereto, followed by maintaining at 37° C. for 5 minutes. Then the mixture was centrifuged at 3,500 rpm for 5 minutes to thereby precipitate solid matters. 0.05 ml of the supernatant was collected and the pH value thereof was adjusted to 5 to 9 with a 0.15 to 0.85M aqueous solution of sodium hydroxide. Thus a specimen was obtained.

The endotoxin contained in the specimen was assayed in the following manner. ENDOSPECY ® (product of Seikagaku Corporation), which is a preparation obtained by removing enzymes reacting with glucans from the limulus amebocyte lysate extract component, was dissolved in 2.2 ml of a 0.2M tris hydrochloride buffer solution (pH 8.0). 0.1 ml of the specimen was added to 0.1 ml of the ENDOSPECY solution, and incubated at 37° C. for 30 minutes. Then 0.5 ml of a 0.04% by weight of sodium nitrite in 0.48N hydrochloric acid solution, 0.5 ml of 0.3% by weight of ammonium sulfamate and 0.5 ml of 0.07% by weight of N-1-naphthylethylenediamine dihydrochloride were successively added thereto under stirring to perform a diazo coupling reaction. The absorbance of the reaction mixture was determined with an spectrophotometer at 545 nm.

Table 1 shows the results of the assay in this Example, wherein the nitric acid concentration was varied, as well as the results of the Comparative Example wherein no endotoxin was added.

In Table 1, the nitric acid concentration (%) means the final concentration. Regarding the assay results, the data of the Comparative Example in which no endotoxin was added were expressed in the absorbance at 545 nm. On the other hand, the data of Example 1 in which the endotoxin was added were expressed in the detection ratio (%) determined by referring the data of Control Example in which the whole blood sample was replaced by physiological saline for injection, and the nitric acid aqueous solution containing Triton X-100 and the aqueous solution of sodium hydroxide were replaced by distilled water for injection, as to 100.

TABLE 1

| Specimen | Nitric acid conc. (w/v %) | Absorbance (adding no endotoxin) | Detection ratio of added endotoxin (%) |
| --- | --- | --- | --- |
| Example 1 and Comparative Example | 0.64 | unable to collect supernatant | unable to collect supernatant |
| | 0.86 | 0.050 | 108 |
| | 1.27 | 0.023 | 107 |
| | 1.68 | 0.020 | 105 |
| | 2.09 | 0.020 | 100 |
| | 2.50 | 0.021 | 100 |
| | 2.91 | 0.020 | 100 |
| | 3.32 | 0.019 | 91 |
| | 3.77 | 0.018 | 82 |
| | 4.18 | 0.019 | 63 |
| Control Example | 0.00 | 0.020 | 100 |

As Table 1 shows, when a concentration of nitric acid was low, no sample could be obtained since the denatured product was poorly precipitated and it was impossible to effect the separation by centrifugation. When the concentration of nitric acid exceeded 3.32%, on the other hand, the detection ratio of the endotoxin was lowered. Thus it has been clarified that limulus test false-positive factors and inhibition factors (false-negative factors) were completely removed from the whole blood sample when a nitric acid concentration ranged from about 0.86 to 2.91% so that the true content of the endotoxin in the whole blood sample could be accurately determined at a high reliability and a high reproducibility.

The fact that the absorbance of the Comparative Example in which no endotoxin was added agrees with that of the Control Example indicates that the limulus test false-positive factors in the whole blood have been completely denatured and removed. Furthermore, the fact that the detection ratio of the endotoxin in the Example in which the endotoxin was added is 100% means that the limulus test inhibition factors in the whole blood have been completely denatured and removed. It is ideal to select such conditions as to make it possible to completely denature and remove these interfering factors simultaneously, which means that the data of the Comparative Example are almost the same as those of the Control Example and the data of the Example are almost 100% (i.e., the endotoxin added in the Example are almost completely detected and recovered). As Table 1 shows, the aforesaid conditions can be achieved when the nitric acid was used at a concentration of from 2.09 to 2.91%.

EXAMPLE 2

0.05 ml of an anticoagulant (heparin) was added to 10 ml of whole blood collected from a healthy subject. Then the whole blood was frozen at −80° C. for a short period and then completely hemolyzed to serve as a whole blood sample.

To 0.1 ml of this whole blood sample was added 0.01 ml of an aqueous solution containing 10 pg of an endotoxin preparation from E. coli UKT-B (National Institute of Hygienic Sciences, Osaka Branch, Osaka, Japan). Subsequently, 0.5 ml of a 0.66M aqueous solution of nitric acid containing Triton X-100 of a definite concentration (from 0 to 0.83% by weight) was added thereto, followed by maintaining at 37° C. for 5 minutes. Then the mixture was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained.

The endotoxin contained in the specimen was assayed in the same manner as in Example 1.

Table 2 shows the results of the assay in Example 2, in which the concentration of Triton X-100 was varied, as well as the results of the Comparative Example, in which no endotoxin was added, and those of Control Example, in which the whole blood was replaced with physiological saline.

Similar to Example 1, the data of the Comparative Example in which no endotoxin as added were expressed in the absorbance at 545 nm. On the other hand, the data of Example 2 in which the endotoxin was added were expressed in the detection ratio (%) determined by referring the data of Control Example as to 100.

TABLE 2

| Specimen | Triton X-100 conc. (w/v %) | Absorbance (adding no endotoxin) | Detection ratio of added endotoxin (%) |
|---|---|---|---|
| Example 2 and Comparative Example | 0 | 0.032 | 57 |
| | 0.08 | 0.024 | 76 |
| | 0.13 | 0.021 | 92 |
| | 0.17 | 0.021 | 100 |
| | 0.20 | 0.021 | 100 |
| | 0.25 | 0.021 | 100 |
| | 0.33 | 0.020 | 89 |
| | 0.42 | 0.020 | 63 |
| | 0.83 | 0.017 | 8 |
| Control Example | 0 | 0.020 | 100 |

Table 2 shows that the supernatant obtained after centrifugation was contaminated with denatured insoluble matters and the detection ratio of the endotoxin was substantially low, when the concentration of Triton X-100 was 0 (i.e., no Triton X-100 was added). In contrast, the supernatant obtained by centrifuging the whole blood sample treated with nitric acid containing, for example, 0.17 to 0.25% of Triton X-100, was a colorless and transparent liquid free from any decomposed and denatured matters. In this case, the added endotoxin was detected at a ratio of 100%.

Thus it has been found that limulus test false-positive factors and inhibition factors were completely removed from the whole blood when the surfactant (Triton X-100) was used in an appropriately predetermined concentration so that the true content of an endotoxin in the whole blood sample could be accurately determined at a high reliability.

In this Example, the case wherein no Triton X-100 was added (i.e., treated with nitric acid alone) corresponds to the acid-treatment described in U.S. Pat. No. 4,495,294 as mentioned above. Thus it is indicated that the present invention has considerably improved the known assay method and thus enables the accurate assay of an endotoxin in whole blood.

EXAMPLE 3

To 0.1 ml of a whole blood sample prepared in the same manner as in Example 2 was added 0.01 ml of an aqueous solution containing 10 pg of an endotoxin preparation from E. coli UKT-B (National Institute of Hygienic Sciences, Osaka Branch, Osaka, Japan). Subsequently, 0.5 ml of a 0.66M aqueous solution of nitric acid containing 0.25% by weight of Triton X-100 was added thereto, followed by maintaining at 37° C. for a definite period of time. Then the mixture was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained.

The endotoxin contained in the specimen was assayed in the same manner as in Example 1.

Table 3 shows the results of the assay in Example 3, in which the heating period was varied, as well as the results of the Comparative Example, in which no endotoxin was added, and those of Control Example, in which the whole blood was replaced with physiological saline.

TABLE 3

| Specimen | Heating time (min.) | Absorbance (adding no endotoxin) | Detection ratio of added endotoxin (%) |
|---|---|---|---|
| Example and Comparative Example | 0 | 0.021 | 66 |
| | 3 | 0.021 | 90 |
| | 5 | 0.021 | 100 |
| | 10 | 0.021 | 100 |
| | 20 | 0.022 | 96 |
| | 30 | 0.022 | 93 |
| Control Example | untreated | 0.020 | 100 |

As shown in Table 3, the detection ratio was low, when the sample was heated for 0 minute (i.e., centrifuged immediately after the treatment with nitric acid and Triton X-100). In contrast, it has been found that limulus test false positive factors and inhibition factors were completely removed from the whole blood sample when the sample was pretreated for 5 minutes or longer so that the true content of an endotoxin in the whole blood sample could be accurately determined at a high reliability.

EXAMPLE 4

To 0.1 ml of a whole blood sample prepared in the same manner as in Example 2 was added 0.01 ml of an aqueous solution containing 10 pg of an endotoxin preparation from E. coli UKT-B (National Institute of Hygienic Sciences, Osaka Branch, Osaka, Japan). Then, 0.5 ml of a 0.66M aqueous solution of nitric acid containing 0.25% by weight of Triton X-100 was added thereto, followed by maintaining at a definite temperature for 5 minutes. Then the mixture was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained.

The endotoxin contained in the specimen was assayed in the same manner as in Example 1.

Table 4 shows the results of the assay in Example 4, in which the heating temperature was varied, as well as the results of the Comparative Example, in which no endotoxin was added, and those of Control Example, in which the whole blood was replaced with physiological saline.

TABLE 4

| Specimen | Heating temp. (°C.) | Absorbance (adding no endotoxin) | Detection ratio of added endotoxin (%) |
|---|---|---|---|
| Example 4 | 4 | 0.021 | 72 |
| and | 25 | 0.021 | 89 |
| Comparative | 37 | 0.021 | 100 |
| Example | 45 | 0.021 | 100 |
|  | 56 | 0.021 | 100 |
|  | 70 | 0.021 | 87 |
|  | 80 | 0.021 | 82 |
| Control Example | untreated | 0.020 | 100 |

As shown in Table 4, the detection ratio was low when the sample was treated at 4° C. In contrast, it has been found that limulus test false-positive factors and inhibition factors were completely removed from the whole blood sample when the sample was treated at 37° C. or above so that the true content of an endotoxin in the whole blood sample could be accurately determined at a high reliability.

EXAMPLE 5

The whole blood collected from a healthy subject without adding any anticoagulant was completely hemolyzed by vigorously stirring to give a whole blood sample.

To 0.1 ml of the whole blood sample thus prepared was added 0.01 ml of an aqueous solution containing 10 pg of a *S. abortus equi* endotoxin (Sigma Chemical Co.). Subsequently, 0.5 ml of a 0.66M aqueous solution of nitric acid containing Tween 20 ® (polyoxyethylene sorbitan monolaurate, product of Wako Pure Chemical Industries, Ltd.) at a definite concentration selected within a range of from 0 to 1.0% was added thereto, followed by maintaining at 37° C. for 5 minutes. Then, the mixture was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained.

The endotoxin contained in the specimen was assayed in the same manner as in Example 1.

Table 5 shows the results of the assay in Example 5, in which the concentration of Tween 20 was varied, as well as the results of the Comparative Example, in which no endotoxin was added, and those of Control Example, in which the whole blood was replaced with physiological saline.

TABLE 5

| Specimen | Tween 20 conc. (w/v %) | Absorbance (adding no endotoxin) | Detection ratio of added endotoxin (%) |
|---|---|---|---|
| Example 5 | 0 | 0.034 | 54 |
| and | 0.08 | 0.025 | 87 |
| Comparative | 0.17 | 0.021 | 98 |
| Example | 0.21 | 0.021 | 100 |
|  | 0.25 | 0.021 | 100 |
|  | 0.33 | 0.020 | 100 |
|  | 0.42 | 0.020 | 100 |
|  | 0.83 | 0.018 | 75 |
| Control Example | 0 | 0.020 | 100 |

From the results shown in Table 5, it was found that limulus test false-positive factors and inhibition factors were completely removed from the whole blood sample when the sample was treated with the surfactant (Tween 20) at an appropriately predetermined concentration so that the true content of an endotoxin in the whole blood sample could be accurately assayed at a high reliability. On the other hand, the sample treated with nitric acid alone without adding any Tween 20 showed an obviously lower detection ratio of the endotoxin.

EXAMPLE 6

To 0.1 ml of the whole blood sample prepared in the same manner as in Example 5 were successively added 0.01 ml of an aqueous solution containing 10 pg of a *S. abortus equi* endotoxin (Sigma Chemical Co.) and 0.5 ml of a 0.66M aqueous solution of nitric acid containing Tween 80 ® (polyoxyethylene sorbitan monooleate, product of Wako Pure Chemical Industries, Ltd) at a definite concentration selected within a range of from 0 to 1.0%. After maintaining at 37° C. for 5 minutes, the mixture was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained.

The endotoxin contained in the specimen was assayed in the same manner as in Example 1.

Table 6 shows the results of the assay in Example 6, in which the concentration of Tween 80 was varied, as well as the results of the Comparative Example, in which no endotoxin was added, and those of Control Example, in which the whole blood was replaced with physiological saline.

TABLE 6

| Specimen | Tween 80 conc. (w/v %) | Absorbance (adding no endtoxin) | Detection ratio of added endotoxin (%) |
|---|---|---|---|
| Example 6 | 0 | 0.032 | 51 |
| and | 0.08 | 0.031 | 67 |
| Comparative | 0.17 | 0.025 | 85 |
| Example | 0.25 | 0.021 | 94 |
|  | 0.33 | 0.021 | 100 |
|  | 0.42 | 0.021 | 100 |
|  | 0.83 | 0.020 | 83 |
| Control Example | 0 | 0.020 | 100 |

From the results shown in Table 6, it was found that limulus test false-positive factors and inhibition factors were completely removed from the whole blood sample when the sample was treated with the surfactant (Tween 80) at an appropriately predetermined concentration so that the true content of an endotoxin in the whole blood sample could be accurately assayed at a high reliability. On the other hand, the sample treated with nitric acid alone without adding any Tween 80 showed an obviously lower detection ratio of the endotoxin.

EXAMPLE 7

To 0.1 ml of a whole blood sample prepared in the same manner as in Example 5 were successively added 0.01 ml of an aqueous solution containing 30 pg of an endotoxin preparation from *E. coli* 0111:B4 (Difco Laboratories, Inc.) and 0.5 ml of a 0.66M aqueous solution of nitric acid containing sodium dodecylsulfate (SDS) at a definite concentration selected within a range of from 0 to 0.83%. After maintaining at 37° C. for 5 minutes, the mixture was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained.

The endotoxin contained in the specimen was assayed in the same manner as in Example 1.

Table 7 shows the results of the assay in Example 7, wherein the SDS concentration was varied, as well as the results of the Comparative Example, wherein no endotoxin was added, and those of Control Example, wherein the whole blood was replaced with physiological saline, similar to Example 1.

TABLE 7

| Specimen | SDS conc. (w/v %) | Absorbance (adding no endotoxin) | Detection ratio of added endotoxin (%) |
|---|---|---|---|
| Example 7 | 0 | 0.035 | 57 |
| and | 0.08 | 0.035 | 60 |
| Comparative | 0.17 | 0.022 | 95 |
| Example | 0.21 | 0.021 | 100 |
|  | 0.25 | 0.021 | 100 |
|  | 0.33 | 0.021 | 100 |
|  | 0.42 | 0.022 | 102 |
|  | 0.83 | 0.019 | 88 |
| Control Example | 0 | 0.020 | 100 |

As shown in Table 7, it was found that limulus test false-positive factors and inhibition factors were completely removed from the whole blood sample when the surfactant (SDS) was used at an appropriately predetermined concentration so that the true content of an endotoxin in the whole blood sample could be accurately assayed at a high reliability.

EXAMPLE 8

The whole blood collected from a healthy subject using sodium ethylenediamine tetraacetate (anticoagulant) was cooled to 4° C. without hemolyzing to thereby give a whole blood sample.

To 0.1 ml of the whole blood sample thus prepared were successively added 0.01 ml of an aqueous solution containing 30 pg of an endotoxin preparation from *E. coli* 0111:B4 (Difco Laboratories) and 0.5 ml of a 0.66M aqueous solution of nitric acid containing n-octylglucopyranoside at a definite concentration selected within a range of from 0 to 1.0%. The mixture was maintained at 37° C. for 5 minutes and then, it was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained.

The endotoxin contained in the specimen was assayed in the same manner as in Example 1.

Table 8 shows the results of the assay in Example 8, in which the concentration of n-octylglucopyranoside was varied, as well as the results of the Comparative Example, in which no endotoxin was added, and those of Control Example, in which the whole blood was replaced with physiological saline.

TABLE 8

| Specimen | n-Octyl-glucopyranoside conc. (w/v %) | Absorbance (adding no endotoxin) | Detection ratio of added endotoxin (%) |
|---|---|---|---|
| Example 8 | 0 | 0.035 | 57 |
| and | 0.08 | 0.030 | 58 |
| Comparative | 0.13 | 0.022 | 72 |
| Example | 0.17 | 0.021 | 85 |
|  | 0.20 | 0.021 | 96 |
|  | 0.25 | 0.021 | 100 |
|  | 0.33 | 0.021 | 100 |
|  | 0.42 | 0.020 | 91 |
|  | 0.83 | 0.015 | 2 |
| Control Example | 0 | 0.020 | 100 |

As shown in Table 8, it was found that limulus test false-positive factors and inhibition factors were completely removed from the whole blood sample when the sample was treated with the surfactant (n-octylglucopyranoside) at a concentration appropriately predetermined so that the true content of an endotoxin in the whole blood sample could be accurately determined at a high reliability.

EXAMPLE 9

The whole bloods of various experimental animals including male ICR mice, male Wistar rats, male Hartley guinea pigs, male JW rabbits and male Beagle canines were collected with adding an anticoagulant (heparin). These whole bloods were frozen at −80° C. within a short period and then completely hemolyzed to thereby give whole blood samples.

To 0.1 ml of each whole blood sample thus prepared, were successively added 0.01 ml of an aqueous solution containing 10 pg of an endotoxin preparation from *E. coli* UKT-B (National Institute of Hygienic Sciences, Osaka Branch, Osaka, Japan) and 0.5 ml of a 0.66M aqueous solution of nitric acid containing 0.5 ml of Triton X-100. The mixture is maintained at 37° C. for 5 minutes and then it was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained.

The endotoxin contained in the specimen was assayed in the same manner as in Example 1.

Table 9 shows the results of the assay in Example 9 as well as the results of the Comparative Example in which no endotoxin was added, and those of Control Example in which the whole blood was replaced with physiological saline.

TABLE 9

| Specimen | Test animal | Absorbance (adding no endtoxin) | Detection ratio of added endotoxin (%) |
|---|---|---|---|
| Example 9 | Mouse | 0.020 | 100 |
| and | Rat | 0.021 | 100 |
| Comparative | Guinea pig | 0.021 | 99 |
| Example | Rabbit | 0.023 | 100 |

TABLE 9-continued

| Specimen | Test animal | Absorbance (adding no endtoxin) | Detection ratio of added endotoxin (%) |
|---|---|---|---|
| | Canine | 0.020 | 99 |
| Control Example | | 0.020 | 100 |

As shown in Table 9, the detection ratio was almost 100% in each animal.

Thus, the assay method of the present invention can provide good results even in the case of using a limited amount of samples obtained from small experimental animals. This means that the method of the present invention is remarkably improved not only in the quickness and convenience but also in the specific treatment of specimens as compared with conventional ones.

REFERENCE EXAMPLE 0.5 ml of an anticoagulant [7.6% (w/v) of sodium citrate] was added to 10 ml of whole blood collected from a healthy subject. Then the whole blood was frozen at −80° C. within a short period and then completely hemolyzed to thereby give a whole blood sample.

To 0.1 ml of the whole blood sample thus prepared were successively added 0.01 ml of an aqueous solution containing 30 pg of an endotoxin preparation from E. coli 0111:B4 (Difco Laboratories, Inc.) and 0.5 ml of a 0.45 to 0.55M aqueous solution of nitric acid. After maintaining at 37° C. for 5 minutes, the mixture was centrifuged at 3,500 rpm for 5 minutes to thereby precipitate solid matters. 0.4 ml of the supernatant was collected and the pH value thereof was adjusted to 5 to 9 with 0.4 ml of a 0.45 to 0.55M aqueous solution of sodium hydroxide. Thus a specimen was obtained.

0.1 ml of the resulting specimen was added to a mixture of limulus amebocyte lysate extract component, a synthetic chromogenic substrate (Boc-Leu-Gly-Arg-pNA), tris hydrochloride buffer (pH 8.0) and Triton X-100 at various concentrations. Then the mixture was maintained at 37° C. for 30 minutes and then the endotoxin was assayed.

Separately, the endotoxin was added to whole blood in the same manner as described above and then 0.5 ml of a 0.66M nitric acid aqueous solution containing Triton X-100 at various concentrations was added thereto. After maintaining at 37° C. for 5 minutes, the mixture was centrifuged at 3,500 rpm for 5 minutes to thereby precipitate solid matters. 0.05 ml of the supernatant was collected and the pH value thereof was adjusted to 5 to 9 with 0.4 ml of a 0.45 to 0.55M solution of sodium hydroxide. Thus another specimen was obtained.

0.1 ml of the resulting specimen was added to a mixture of the limulus amebocyte lysate extract component, a synthetic chromogenic substrate (Boc-Leu-Gly-Arg-pNA) and tris hydrochloride buffer (pH 8.0). Then the mixture was incubated at 37° C. for 30 minutes and then the absorbance thereof at 545 nm was measured with a spectrophotometer in the same manner as in Example 1. Table 10 shows the results.

In Table 10, the data of the Comparative Example, in which no endotoxin was added were expressed in the absorbance at 545 nm. On the other hand, the data of the Reference Example, in which the endotoxin was added, were expressed in the detection ratio (%) determined by referring the data of Control Example, in which the whole blood sample was replaced by physiological saline for injection, as to 100. the Triton X-100 concentration (w/v %) means the concentration in the assay system.

TABLE 10

| Specimen | Triton X-100 conc. (w/v %) | Adding Triton X-100 after treating with at nitric acid | | Adding nitric acid containing Triton X-100 | |
|---|---|---|---|---|---|
| | | Absorbance (adding no endotoxin) | Endotoxin detection ratio (%) | Absorbance (adding no endotoxin) | Endotoxin detection ratio (%) |
| Reference and Comparative Examples | 0 | 0.032 | 55 | 0.032 | 55 |
| | 0.001 | 0.032 | 55 | 0.032 | 55 |
| | 0.003 | 0.032 | 69 | 0.032 | 59 |
| | 0.005 | 0.034 | 70 | 0.029 | 61 |
| | 0.010 | 0.030 | 51 | 0.026 | 72 |
| | 0.020 | 0.020 | 8 | 0.024 | 81 |
| | 0.025 | 0.017 | 0 | 0.021 | 93 |
| | 0.033 | 0.017 | 0 | 0.021 | 100 |
| | 0.043 | 0.016 | 0 | 0.021 | 100 |
| | 0.050 | 0.016 | 0 | 0.021 | 100 |
| | 0.063 | 0.015 | 0 | 0.021 | 100 |
| | 0.082 | 0.015 | 0 | 0.021 | 100 |
| | 0.105 | 0.015 | 0 | 0.020 | 65 |
| | 0.208 | 0.014 | 0 | 0.017 | 7 |
| Control Example | 0 | 0.020 | 100 | 0.020 | 100 |

From the results shown in Table 10, its was found that the endotoxin could not be determined when the specimen was treated with nitric acid and then a surfactant such as Triton X-100 was added to the limulus amebocyte lysate component at the enzyme reaction and that the addition of the surfactant at a definite concentration or above at the enzyme reaction caused serious inhibition. It has been furthermore found that the sample was considerably colored due to hemolysis and the assay-inhibition factors could not be removed at all, when a surfactant such as Triton X-100 was added without adding nitric acid followed by heating (under the same conditions as those described above except that the sodium hydroxide employed for neutralization was replaced by water). In this case, therefore, the blank value was extremely high and the added endotoxin was never recovered. On the other hand, according to the assay method of the present invention in which a whole blood sample is simultaneously treated with a surfactant such as Triton X-100 and nitric acid, the endotoxin can be accurately determined.

EXAMPLE 10

10 μl portions of a 40 ng/ml aqueous solution of E. coli 0111:B4 endotoxin (Difco Laboratories, Inc.) were added to 90 μl portions of trypsin (bovine pancreas, 1 mg/ml, Sigma), thrombin (human plasma, 250 units/ml, Mochida Pharmaceutical Co., Ltd.) and plasmin (human plasma, 25 units/ml, Sigma) and well stirred. 90 μl of a human whole blood sample prepared in the same manner as in Example 1 was added to 10 μl of each mixture as prepared above and further mixed. Subsequently, 0.5 ml of a 0.66M aqueous solution of nitric acid containing 0.25% by weight of Triton X-100 was added thereto, followed by maintaining at 37° C. for 5 minutes. Then the mixture was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained. The endotoxin contained in the specimen was assayed in the same manner as in Example 1.

Table 11 shows the results of the assay of Example 10, in which the concentration of the protease were varied, as well as the results of the Comparative Example, in which no endotoxin was added (untreated and treated), and those of Control Example, wherein the whole blood was replaced with physiological saline, similar to Example 1.

As shown in Table 11, it was found that limulus test false-positive factors and inhibition factors contained in a protease solution were completely removed when the whole blood was added to a protease solution and then treated with nitric acid containing a surfactant at an appropriately predetermined concentration so that the true content of an endotoxin in the sample could be accurately determined at a high reliability.

TABLE 11

| Specimen | Protease Kind | Conc. (/ml) | Untreated Absorbance (adding no endotoxin) | Treated Absorbance (adding no endotoxin) | Endotoxin detection ratio (%) |
| --- | --- | --- | --- | --- | --- |
| Example 10 and Comparative Example | trypsin thrombin plasmin | 8.3 μg 2.1 U 0.2 U | 1.500 0.290 0.205 | 0.035 0.026 0.020 | 100 94 95 |
| Control Example | | | | 0.020 | 100 |

EXAMPLE 11

10 μl portions of a 40 ng/ml aqueous solution of E. coli 0111:B4 endotoxin (Difco Laboratories, Inc.) were added to 90 μl portions of a protease inhibitor, FOY (gabexate mesylate, 1 mg/ml, Ono Pharmaceutical Co., Ltd.), antithrombin III (4 mg/ml, Sigma) and $\alpha_1$-antitrypsin (5 mg/ml, Sigma) and well stirred. 90 μl of a rabbit whole blood sample prepared in the same manner as in Example 9 was added to 10 μl of each mixture as prepared above, and further mixed. Subsequently, 0.5 ml of a 0.66M aqueous solution of nitric acid containing 0.25% by weight of Triton X-100 was added thereto, followed by maintaining at 37° C. for 5 minutes. Then the mixture was centrifuged at 3,500 rpm for 5 minutes to thereby precipitate solid matters. 0.05 ml of the supernatant was collected and the pH value thereof was adjusted to 5 to 9 with a 0.45 to 0.55M aqueous solution of sodium hydroxide. Thus a specimen was obtained. The endotoxin contained in the specimen was assayed in the same manner as in Example 1.

Table 12 shows the results of the assay of Example 11, in which the concentrations of the protease inhibitors were varied, as well as the results of the Comparative Example, in which no endotoxin was added (untreated and treated), and those of Control Example, in which the whole blood was replaced with physiological saline.

As shown in Table 12, it was found that limulus test false-positive factors and inhibition factors contained in the protease inhibitors were completely removed when whole blood was added to protease inhibitors and then treated with nitric acid containing a surfactant at an appropriately predetermined concentration so that the true content of an endotoxin in the sample could be accurately determined at a high reliability.

TABLE 12

| Specimen | Protease Inhibitor Kind | Conc. (/ml) | Untreated Absorbance (adding no endotoxin) | Treated Absorbance (adding no endotoxin) | Endotoxin detection ratio (%) |
| --- | --- | --- | --- | --- | --- |
| Example 11 and Comparative Example | FOY antithrombin III $\alpha^1$-antitrypsin | 8.3 U 33.3 μg 41.6 μg | 0.020 0.019 0.020 | 0.019 0.020 0.020 | 92 100 100 |
| Control Example | | | 0.020 | | 100 |

While the invention has been described in detail and with reference to specific examples thereof, it will be apparent to one skilled in the art that various changes and modifications can be made therein without departing from the spirit and scope thereof.

What is claimed is:

1. A method of assaying an endotoxin in a whole blood sample or a protein solution containing a whole blood sample, using a limulus amebocyte lysate component comprising the steps of:
   (a) obtaining a whole blood sample or a protein solution comprising a whole blood sample;
   (b) treating said sample or solution, prior to contacting with the limulus amebocyte lysate component, by incubating said sample or solution in the presence of both nitric acid and a surfactant, separating the resulting precipitate, and collecting the supernatant, wherein the surfactant is selected from the group consisting of polyethylene glycol mono-p-iso-octylphenyl ether, polyethylene glycol mono-p-tert-octylphenoxypolyethoxyethanol, polyethylene glycol mono(nonylphenyl) ether, polyoxyethylene sorbitan monolaurate, polyoxyethylene sorbitan monopalmitate, polyoxyethylene sorbitan monostearate, polyoxyethylene sorbitan monooleate, polyoxyethylene sorbitan trioleate, n-octyl-α-D-glucopyranoside, n-octyl-β-D-glucopyranoside, n-nonyl-α-D-glucopyranoside, n-nonyl-β-D-glucopyranoside n-dodecyl-α-D-glucopyranoside, n-dodecyl-β-D-glucopyranoside, n-decyl-α-D-glucopyranoside, n-decyl-β-D-glucopyranoside, n-heptyl-α-D-glucopyranoside, n-heptyl-β-D-glucopyranoside, sodium dodecylsulfate and lithium dodecylsulfate; and
   (c) assaying for endotoxin using the resulting treated sample or solution and the limulus amebocyte lysate component.

2. The method of assaying an endotoxin as claimed in claim 1, wherein nitric acid is used in a concentration of 0.28 to 0.83 mol/l.

3. The method of assaying an endotoxin as claimed in claim 1, wherein the treatment of the sample or solution with nitric acid and a surfactant, prior to contacting with the limulus amebocyte lysate component, is carried out at 25° to 70° C.

4. The method of assaying an endotoxin as claimed in claim 1, wherein the treatment of the sample or solution with nitric acid and a surfactant, prior to contacting with the limulus amebocyte lysate component, is carried out for 3 to 30 minutes.

5. The method of assaying an endotoxin as claimed in claim 1, wherein the whole blood sample is selected from the group consisting of human, bovine, equine, canine, sheep, goat, rabbit, rat, guinea pig and mouse blood.

6. The method of assaying an endotoxin as claimed in claim 1, wherein the sample or solution is treated with the surfactant and then with nitric acid.

7. The method of assaying an endotoxin as claimed in claim 1, wherein the sample or solution is treated with the surfactant and nitric acid simultaneously.

8. The method of assaying an endotoxin as claimed in claim 1, wherein the sample or solution is treated with a nitric acid solution containing the surfactant.

* * * * *